United States Patent [19]
Barnhart

[11] Patent Number: 5,250,283
[45] Date of Patent: Oct. 5, 1993

[54] ORGANIC CONTRAST AGENT ANALOG AND METHOD OF MAKING SAME

[75] Inventor: James L. Barnhart, Encinitas, Calif.

[73] Assignee: Molecular Biosystems, Inc., San Diego, Calif.

[21] Appl. No.: 853,100

[22] Filed: Mar. 18, 1992

Related U.S. Application Data

[63] Continuation of Ser. No. 500,471, Mar. 28, 1990, Pat. No. 5,143,715.

[51] Int. Cl.$^5$ ............................................. A61K 31/195
[52] U.S. Cl. .......................................... 424/5; 562/456
[58] Field of Search ............................. 424/5; 560/456

[56] References Cited

U.S. PATENT DOCUMENTS

| | | | |
|---|---|---|---|
| 3,446,837 | 5/1969 | Wallingford | 424/5 |
| 3,842,124 | 10/1974 | Felder et al. | 424/5 |
| 3,856,853 | 12/1974 | Ackerman | 424/5 |
| 3,883,578 | 5/1975 | Gries | 424/5 |
| 4,073,879 | 2/1978 | Long | 424/5 |
| 4,094,966 | 6/1978 | Tilly et al. | 424/5 |
| 4,125,709 | 11/1978 | Smith | 424/5 |
| 4,132,731 | 1/1979 | Klieger et al. | 424/5 |
| 4,160,015 | 7/1979 | Wiegert | 424/5 |
| 4,395,391 | 7/1983 | Pfeiffer et al. | 424/5 |
| 4,474,747 | 10/1984 | Dimo et al. | 424/5 |
| 4,612,185 | 9/1986 | Dean | 424/2 |
| 4,913,853 | 4/1990 | Hoey | 562/113 |
| 4,951,673 | 8/1990 | Long | 128/653 |
| 5,116,599 | 5/1992 | Rogers et al. | 424/9 |

*Primary Examiner*—James H. Reamer
*Attorney, Agent, or Firm*—Tilton, Fallon, Lungmus & Chestnut

[57] ABSTRACT

An organic contrast agent analog is derived to contain fluorine moieties. A method for making the organic contrast agent analog includes the steps of fluorinating the contrast agent analog for increasing the acidity of the analog to increase the choleretic activity of the analog and to render it less toxic.

1 Claim, 5 Drawing Sheets

ORGANIC CONTRAST AGENT ANALOG AND METHOD OF MAKING SAME

This is a continuation of U.S. patent application Ser. No. 07/500,471, filed Mar. 28, 1990, now U.S. Pat. No. 5,143,715.

TECHNICAL FIELD

The present invention relates to organic contrast agent analogs and methods of making the analogs. More particularly, the present invention relates to a method of decreasing the toxicity of such agents through chemical modification.

BACKGROUND ART

In general, current cholangiographic agents used as biliary X-ray contrast agents are now considered too toxic to meet risk/benefit criteria for routine use as contrast agents to visualize the biliary system. Because of the relative toxicity of these agents, these agents are being replaced in use by alternative imaging methodologies, such as ultrasound and magnetic resonance imaging (MRI). On the other hand, the resolution achievable with X-ray radiology techniques is superb. Accordingly, biliary contrast agents can still be quite useful.

A second issue with regard to these agents is the low rate of choleresis associated with biliary excretion of the agent. The low rate of choleresis increases the biliary concentration and thus increases the toxicity.

Current biliary X-ray contrast agents have amphophilic properties. These agents have a hydrophilic head portion; that is, the —CO$_2$H terminus, and a hydrophobic tail; that is, triiodo aniline moiety with an unsubstituted 5-position. Because of this property, they are excreted nearly exclusively by the biliary route. Typical of most amphilphilic molecules, these biliary contrast agents tend to self associate. This property is reflected by the low critical micellar concentration and low osmolalities of their aqueous salt solution.

It is therefore desirable to produce a less toxic and more choleretic contrast agent.

SUMMARY OF THE INVENTION

In accordance with the present invention, there is provided an organic contrast agent analog wherein the analog is an oral or intravenous media having the formula I:

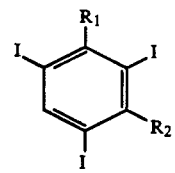

|  | R$_1$ | R$_2$ |
|---|---|---|
| Iopanoic acid | —CH$_2$CH(CH$_2$CH$_3$)COOH | —NH$_2$ |
| Ipodatic acid | —CH$_2$CH$_2$COOH | —N=CHN(CH$_3$)$_2$ |
| Tyropanoic acid | —CH$_2$CH(CH$_2$CH$_3$)COOH | —NHCOCH$_2$CH$_2$CH$_3$ |
| Iocetamic acid | —NCH$_2$CH(CH$_3$)COOH (N-COCH$_3$) | —NH$_2$ |
| Iopronic acid | —OCH$_2$CH$_2$OCH$_2$CH(CH$_2$CH$_3$)COOH | —NHCOCH$_3$ |
| Iosumetic acid | —N(CH$_2$CH$_3$)COCH$_2$CH$_2$COOH | —NHCH$_3$ | or wherein said analog is an intravenous media having formula II;

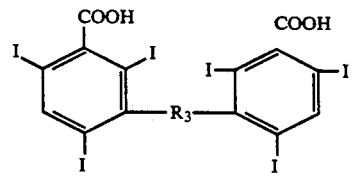

and R$_3$ is

| | R$_3$ |
|---|---|
| Iodipamide | —NHCO(CH$_2$)$_4$CONH— |
| Ioglycamide | —NHCOCH$_2$—O—CH$_2$CONH— |
| Iodoxamate | —NHCO(CH$_2$CH$_2$O)$_4$CH$_2$CH$_2$CONH— |
| Iotroxamide | —NHCO(CH$_2$OCH$_2$)$_3$CONH— |

| | $R_3$ |
|---|---|
| Iosulamide* | $-NHCOCH_2CH_2SO_2CH_2CH_2CONH-$ |

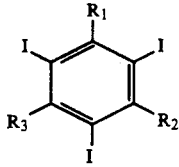
* $-N$ at position 5 or wherein said analog is an urographic media having formula III;

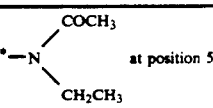

wherein the analog includes one or more fluorine substitutions or additions.

The present invention further provides a method of making the organic contrast agent analog including the steps of forming the organic contrast agent analog having formulas I, II, or III and substituting or adding at least one flourine moiety to the analog.

FIGURES IN THE DRAWINGS

Other advantages of the present invention will be readily appreciated as the same becomes better understood by reference to the following detailed description when considered in connection with the accompanying drawings wherein.

DESCRIPTION OF THE INVENTION

Figure 1:
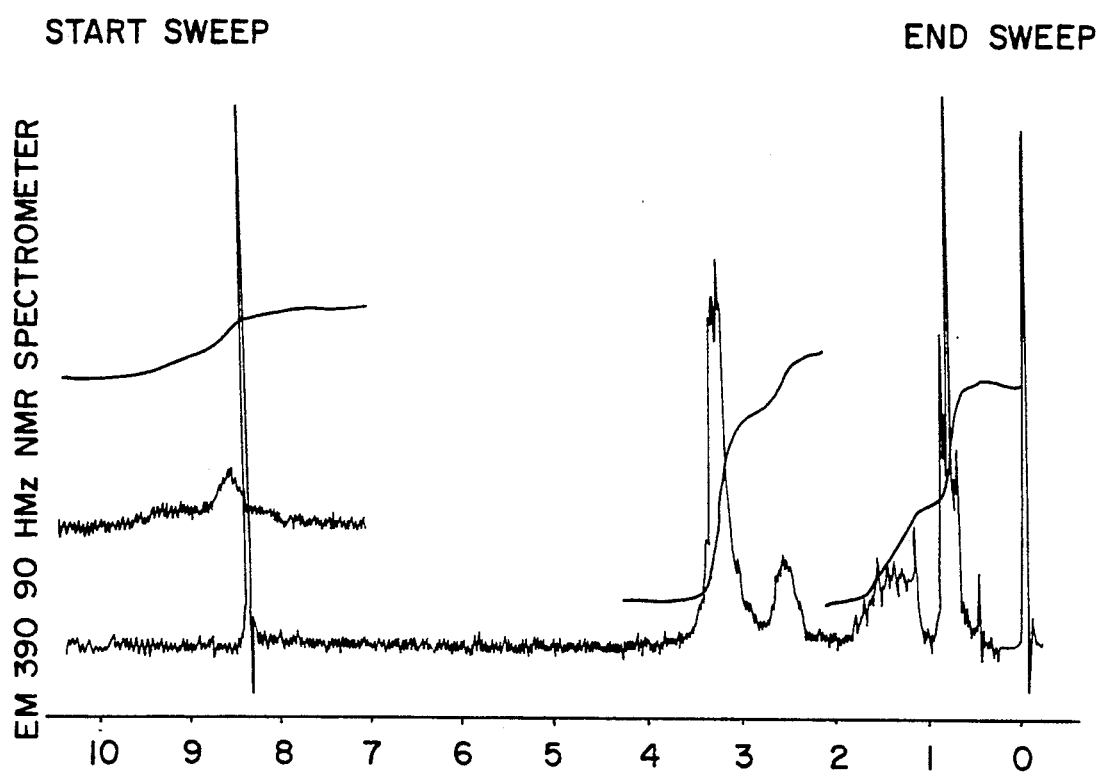
FIGS. 1 and 2 are high resolution NMR proton spectrums.

Generally, an organic contrast agent analog made in accordance with the present invention has the following general formula I:

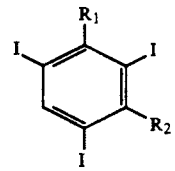

and $R_1$ and $R_2$ are

| | $R_1$ | $R_2$ |
|---|---|---|
| Iopanoic acid | $-CH_2CH\begin{smallmatrix}CH_2CH_3\\COOH\end{smallmatrix}$ | $-NH_2$ |
| Ipodatic acid | $-CH_2CH_2COOH$ | $-N=CHN(CH_3)_2$ |
| Tyropanoic acid | $-CH_2CH\begin{smallmatrix}CH_2CH_3\\COOH\end{smallmatrix}$ | $-NHCOCH_2CH_2CH_3$ |
| Iocetamic acid | $-NCH_2CHCH_3\begin{smallmatrix}COCH_3\\COOH\end{smallmatrix}$ | $-NH_2$ |
| Iopronic acid | $-OCH_2CH_2OCH_2CH\begin{smallmatrix}COOH\\CH_2CH_3\end{smallmatrix}$ | $-NHCOCH_3$ |
| Iosumetic acid | $-N\begin{smallmatrix}CH_2CH_3\\COCH_2CH_2COOH\end{smallmatrix}$ | $-NHCH_3$ | or wherein said analog is an intravenous media having the formula II;

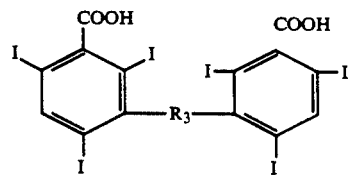

and $R_3$ is

| | $R_3$ |
|---|---|
| Iodipamide | $-NHCO(CH_2)_4CONH-$ |
| Ioglycamide | $-NHCOCH_2-O-CH_2CONH-$ |
| Iodoxamate | $-NHCO(CH_2CH_2O)_4CH_2CH_2CONH-$ |
| Iotroxamide | $-NHCO(CH_2OCH_2)_3CONH-$ |

| | $R_3$ |
|---|---|
| Iosulamide* | —NHCOCH₂CH₂SO₂CH₂CH₂CONH— |

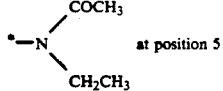

or wherein said analog is an urographic media having the formula III;

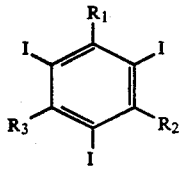

The agent includes a hydrophilic head (side chain) and a hydrophilic tail (benzine ring). The fluorine addition or substitution provides means for increasing the acidity of the agent and increasing the choleretic activity of the agent to render the agent less toxic.

Examples of oral cholecystographic contrast media which can be modified in accordance with the present invention are

TABLE 1

| Common name | proprietary name | Manufacturer | Molecular weight(m.w.) Acid form | Molecular weight(m.w.) Salt form | Iodine (%/m.w.) |
|---|---|---|---|---|---|
| Iopanoic acid | Telepaque | Winthrop | 571 | | 66.7 |
| Ipodate.calcium | Oragratin.calcium | Squibb | 598 | 1.234 | 63.7 |
| Ipodate.sodium | Oragratin.sodium | Squibb | 598 | 620 | 63.7 |
| Tyropanoate.sodium | Bilopaque | Winthrop | 641 | 663 | 59.4 |
| Iocetamic acid | Cholebrine | Mallinckrodt | 614 | | 62.0 |
| Iopronic acid | Oravue | Squibb | 673 | | 56.6 |
| Iosumetic acid | | Schering | 628 | | 60.6 |

Examples of intravenous cholangiographic media modifiable in accordance with the present invention are

TABLE 2

| N-Methylglucamine salt or contrast media | Proprietary name | Manufacturer | Molecular weight(m.w.) Acid form | Molecular weight(m.w.) Salt form | Iodine (%/m.w.) |
|---|---|---|---|---|---|
| Iodipamide | Chologratin | Squibb | 1.140 | 1.530 | 66.8 |
| Ioglycamide | Biligram | Schering | 1.128 | 1.518 | 67.5 |
| Iodoxamate | Cholevue | Winthrop | 1.288 | 1.678 | 59.1 |
| Iotroxamide | | Schering | 1.316 | 1.706 | 57.9 |
| Iosulamide | | Winthrop | 1.376 | 1.764 | 55.3 |

More specifically, the starting agent can be a cholangiographic or cholecystographic agent as stated above. The agent can be of the oral or intravenous types. That is, the agent is iodinated such that it can be used as a biliary X-ray contrast agent for routine use to visualize hepatocytes gallbalder and the the biliary system. Unlike previously used cholecystographic agents, such as underivatized iopanoic acid, the present invention is a chemically modified organic contrast agent analog which is rendered less toxic and more choleretic by the modification of the agent including additional fluorine functionalities on the agent, the fluorine functionalities rendering the agent more acidic and more choleretic.

It has been hypothesized that if an amphophilic molecule, such as a common organic contrast agent analog is rendered a stronger acid and is fully or at least more disassociated at physiological pH, it will most likely be excreted unconjugated, without causing choloresis and without being trapped in the intrahepatic shunt pathway (Sawkat, MS. et al; Influence of side-chain charge on hepatic transport of bile acids and bile acid analogues. American Journal Physiology 249:G479–G488, 1985; Gurantz D., et al; Influence of bile acid structure on bile flow and biliary lipid secretion in the hamster. American Journal Physiology 247:G738–G748, 1984; Yoon, YB, et al, Effect of side-chain shortening on the physiologic properties of bile acids: hepatic transport and effect on biliary sectetion of 23-nor-ursodeoxycholate in rodents. Gastroenterology 90:837–852, 1986). Even in the presence of choleresis, if the hepatocyte and canalicular transport steps are rapid, the biliary contrast agent is expected to move as a bolus, and anatomical details, such as the intrahepatic ducts, can be visualized in patients with good hepatocyte function.

For example, the agent can be N-trifluoroacetyl-iopanoic acid or alpha-fluoro-N-trifluoroacidic-iopanoic acid.

The present invention further provides a method of making the organic contrast agent analog. The method generally includes the steps of forming the organic contrast agent analog having the formulas I, II, or III and then increasing the acidity of the agent while increasing the choleretic activity of agent to render the agent less toxic by adding or subtituting flourine on the agent.

EXPERIMENTS

1. Synthesis of N-trifluoro Derivative of Iopanoic Acid

Three fluorine atoms were attached to the cholecystographic agent iopanoic acid (IOP) so that it could be detected using 19-F magnetic resonance techniques.

IOP was reacted with trifluoroacetic anhydride at 0° C. in tetrahydrofuran. After the reaction was complete, the organic solvents were removed. The residue was dissolved in ethyl acetate and washed twice with water. The organic layer was dried over magnesium sulphate and the solvent was removed to obtain the final product. The product, N-trifluorcacetyl iopanoic acid, had a melting point of 193° C. and an extension coefficient of approximately 37,000 at 232 nm. The assigned structure was verified using high resolution proton and fluorine NMR spectroscopy, elemental analysis and mass spectrum analysis. The isolated yield of the product was 97.5%.

The following summarizes the reaction.

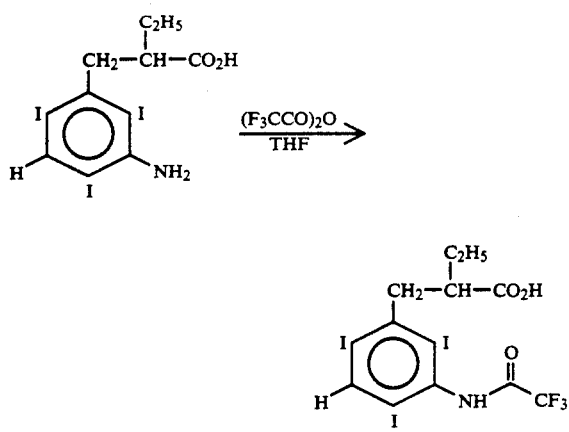

2. Synthesis of Alpha-fluoro-N-trifluoroacetyl-Iopanoic Acid

Functional groups were placed on the carbon atom alpha to the carboxyl group of the organic contrast agent, iopanoic acid. A fluorine atom was placed on the carbon atom alpha to the carboxyl group of N-trifluoroacetyl-iopanoic acid to significantly effect its pKa and thus, effect its biodistribution and metabolism. The following summarizes the synthesis of the alpha-fluoro-N-trifluoroacetyliopanoic acid.

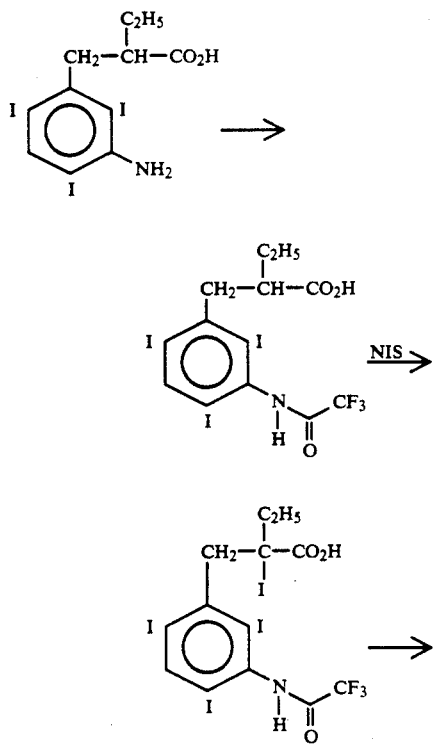

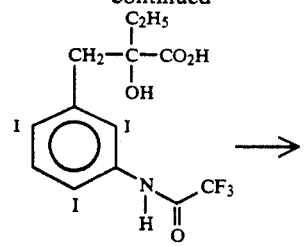

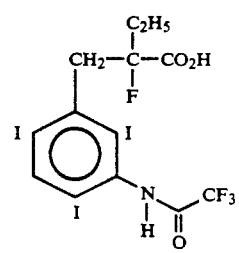

Results of elemental analysis of TFA-IOP provided by Galbraith Laboratories, Inc., Knoxville, Tenn. are as follows:

|   | Galbraith | Theoretical | Error |
|---|-----------|-------------|-------|
| C | 24.33%    | 24.03%      | +0.30% |
| H | 1.93%     | 2.15%       | −0.22% |
| N | 2.04%     | 2.00%       | +0.04% |
| F | 8.50%     | 8.15%       | −0.35% |
| I | 55.24%    | 54.51%      | +0.73% |
| O |           | 9.16%       |        |
|   |           | 100.0%      |        |

The calculations are based on the inclusion of a molecule of methanol with each molecule of TFA-IOP.

Figure 2:
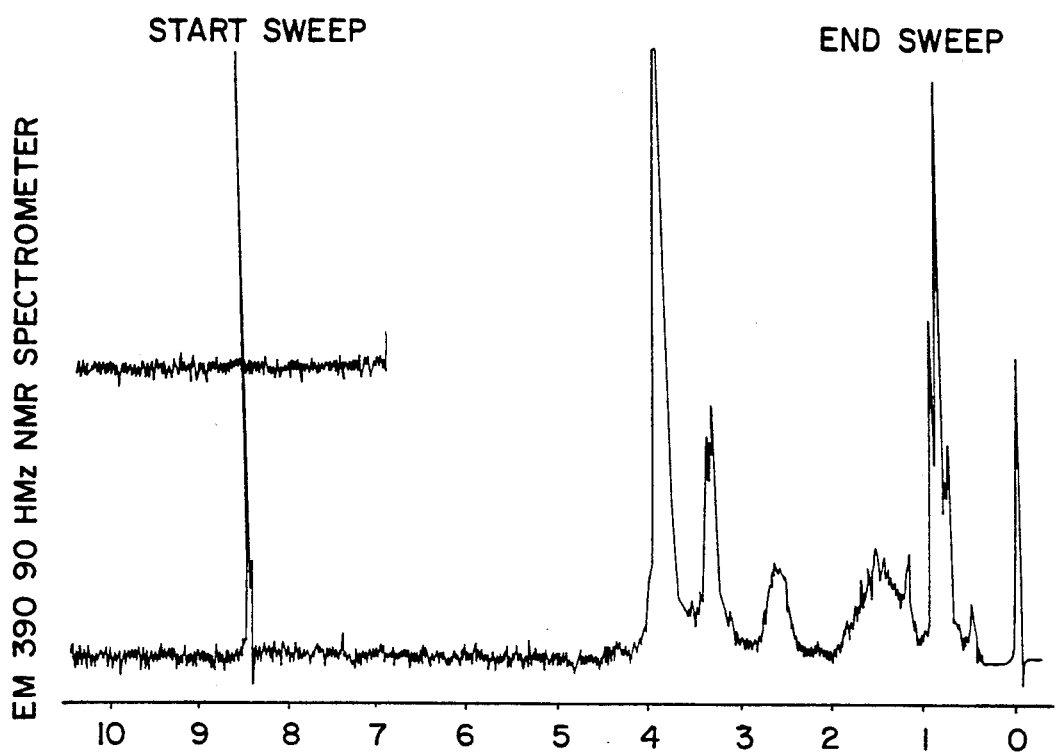
Figure 3:
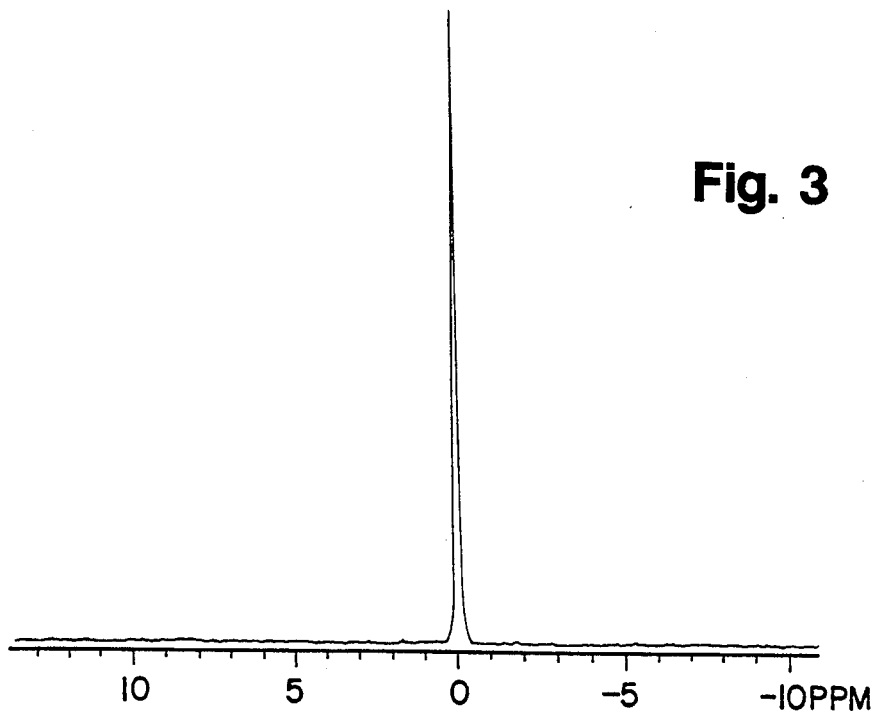
FIG. 3 is a high resolution NMR fluorine spectrum.
Figure 4:
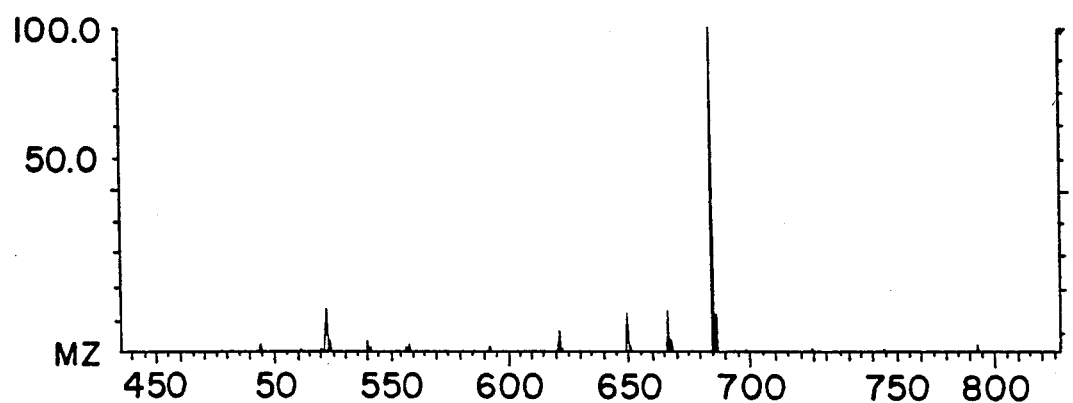
FIGS. 4 and 5 are mass spectrum analyses performed on TFA-IOP made in accordance with the present invention.
Figure 5:
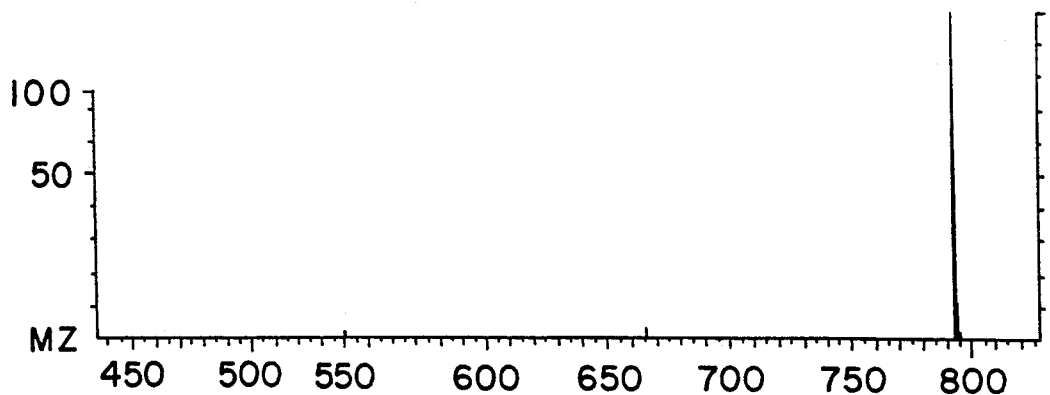

High resolution NMR proton spectrums (FIGS. 1 and 2), high-resolution NMR fluorine spectrum (FIG. 3) and mass spectrum analyses (FIGS. 4 and 5) were performed on TFA-IOP. The results of each confirm the expected chemical structure of the new compound. Mass spectral analysis was performed.

3. Comparative Data of Biliary Excretion of IOP and Trifluoroacetyl IOP

Experiments were conducted to compare the biodistribution and excretion of TFA-IOP to that of the parent compound IOP. TFA-IOP and IOP were each administered intravenously to rats (100 umol/kg) in order to compare the biodistribution and excretion of the compound made in accordance with the present invention and the parent compound. Tissues examined included liver, spleen, upper GI, lower GI, kidney, lung and heart. The length of each study was 90 minutes, during which time bile, urine and plasma samples were taken to monitor uptake and excretion. NMR relaxation rates for liver and plasma were also examined to note whether uptake of either compound might possible alter these parameters.

4. Results

Figure 6:
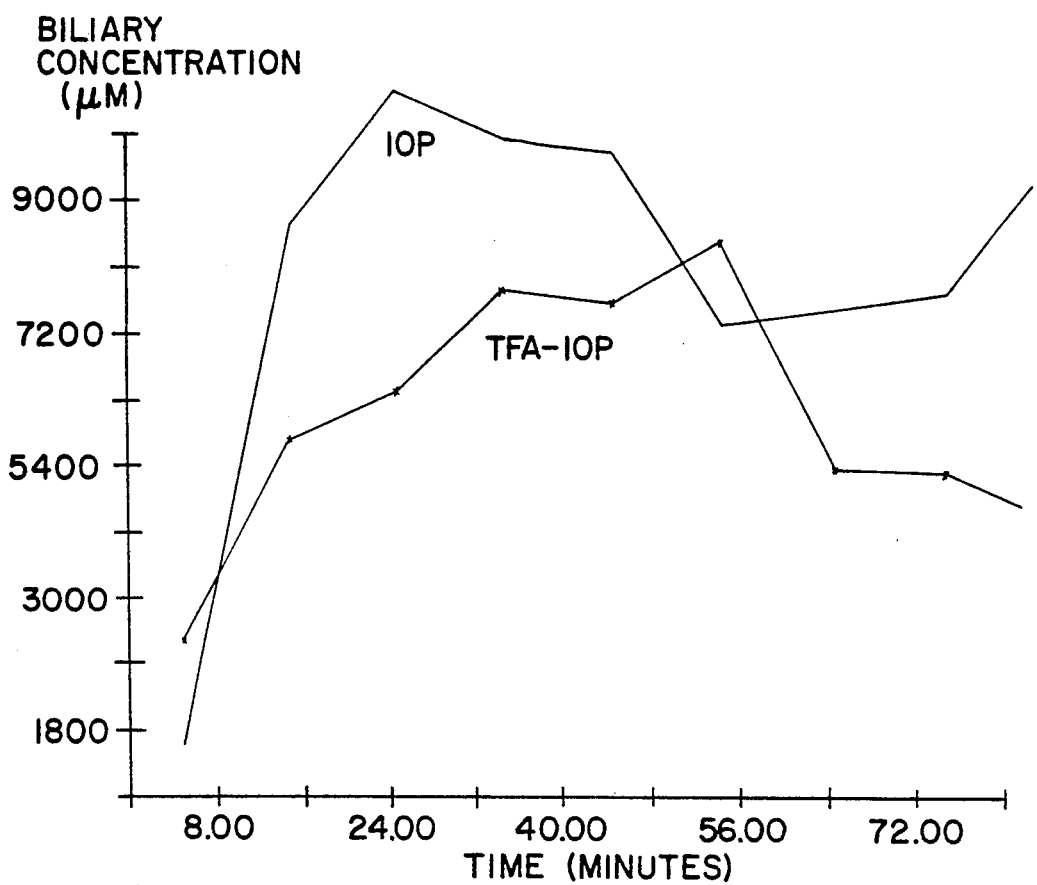
FIG. 6 is a plotted curve comparing biliary concentration over time of IOP versus TFA-IOP.
Figure 7:
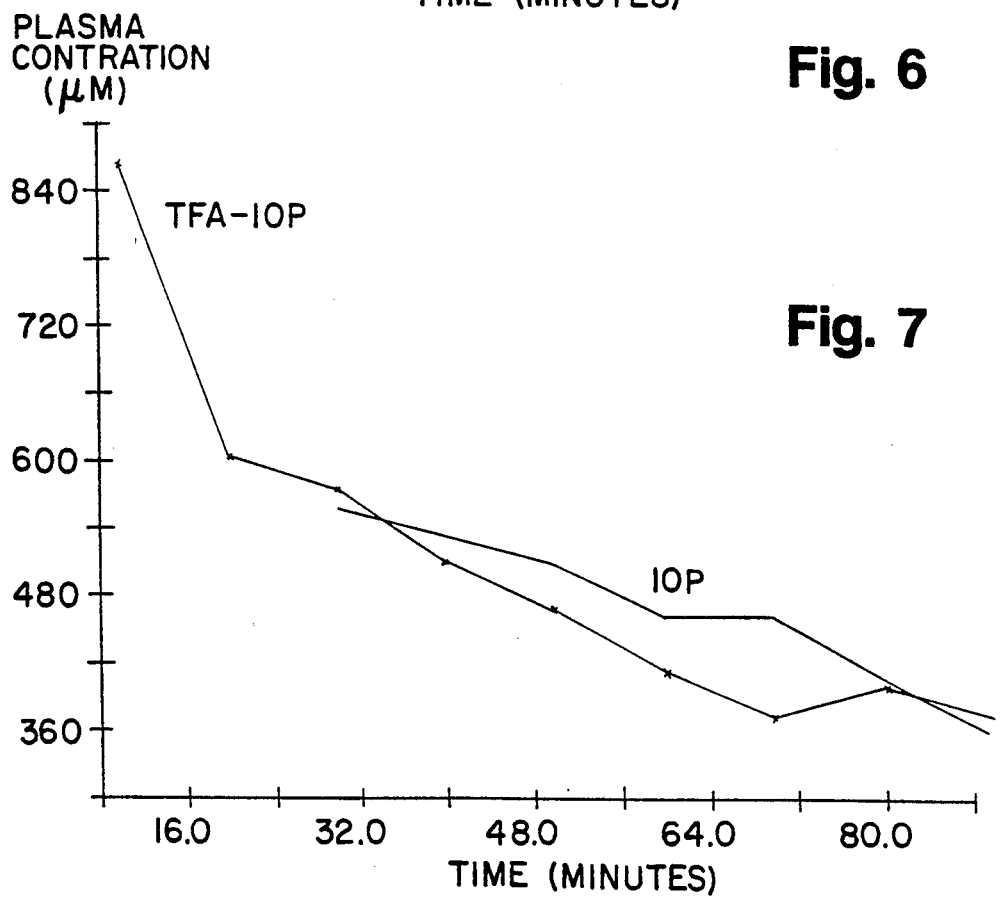
FIG. 7 is comparative data of TFA-IOP and IOP plasma concentration versus time.

In general, liver concentrations 90 minutes post injection were 512 uM and 202 uM after IOP and TFA-IOP injection, respectively, while kidney concentrations were 105 uM and 5 uM. Lesser concentrations were found in the other tissues. Excretion of the two compounds were found only in bile with no compound detected in urine. In bile, TFA-IOP reached a maximum concentration of 0.5 uM with the recovery of 40% of the injection dose during a 90 minute time period (see FIG. 6). For IOP, the biliary concentration reached 10 mM with 18% of the injected does recovered during the 90 minute collection period as shown in FIG. 6. Plasma disappearance curves were similar in form, as shown in FIG. 7. Thin layer chromatoqraphy of bile indicated that a vast majority of the injected TFA-IOP was metabolized to a single metabolite. No nonmetabolized compound was found.

Figure 8:
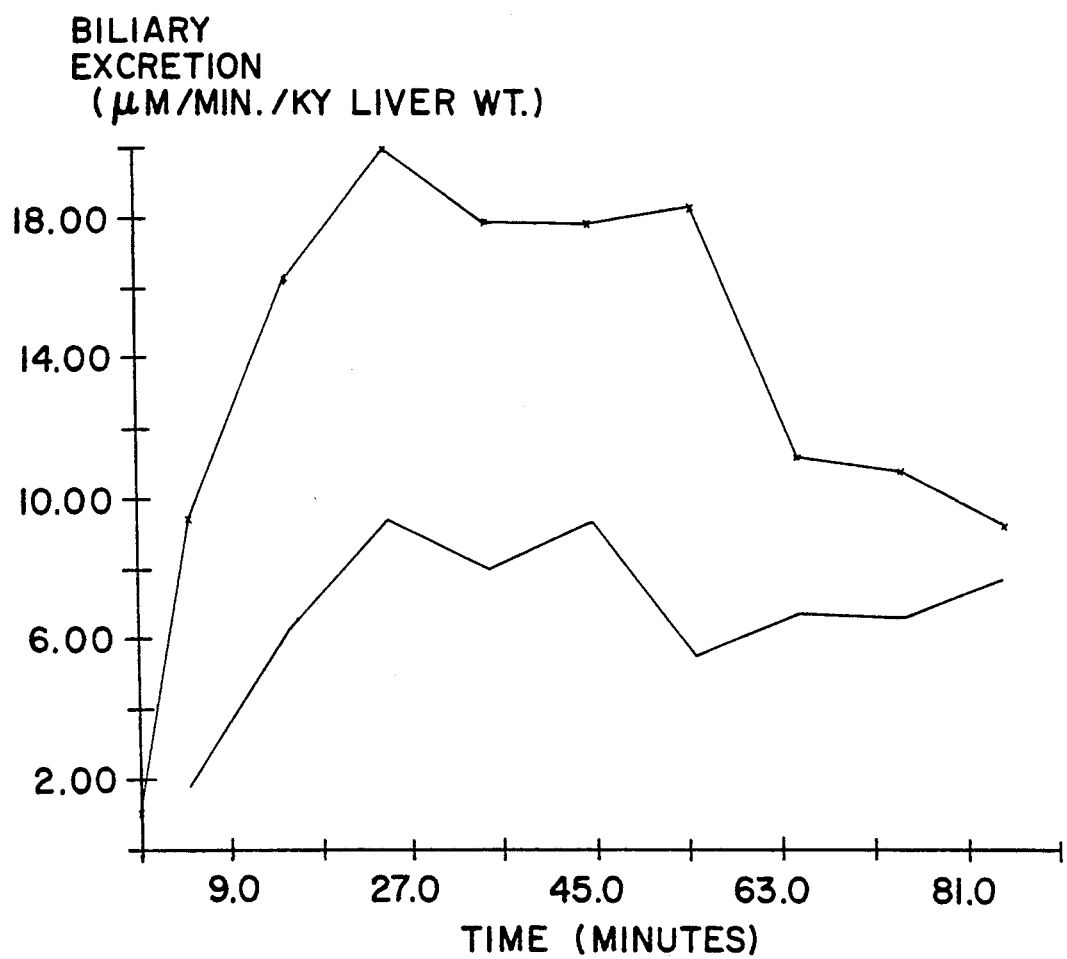
FIG. 8 is a comparative date of TFA-IOP and IOP biliary excretion concentration versus time.

These results indicate that TFA and IOP are similar to their biodisposition except the rate of biliary excretion of TFA-IOP appears to be approximately twice that of IOP, as shown in FIG. 8.

Tables 1 through 5 summarizes the results of each experiment conducted. Table 6 shows a more detailed analysis of the tissue concentration results with values such as total micromoles in tissue, percent of dose/gm, etc.

Tables 7 and 8 contain analysis of the bile excretion results.

TABLE 1

TISSUES:
−IOP CONCENTRATION (uM)
90 MIN POST INJECTION

| | I-6 (IOP) | % OF DOSE | I-8 (TFA-IOP) | % OF DOSE |
|---|---|---|---|---|
| LIVER | 511.90 | 14.53 | 201.73 | 6.04 |
| KIDNEY | 105.40 | 0.69 | 57.84 | 0.34 |
| *UPPER GI | 307.81 | 1.31 | 140.23 | 0.41 |
| *LOWER GI | 135.23 | 0.59 | 178.09 | 0.63 |
| *SPLEEN | 255.54 | 0.45 | 164.06 | 0.24 |
| *LUNG | 324.91 | 1.21 | 277.64 | 0.83 |
| *HEART | 259.38 | 0.72 | 242.85 | 0.72 |

No standard curves were compiled for these tissues. The values given represent concentrations generated using the LIVER analysis routine and standard curve. Because this routine utilizes a control LIVER spectra for background modeling, erroneous Iodine concentration values for these tissues may result due to inappropriate background removal.

TABLE 2

PLASMA:
−IOP CONCENTRATION (uM)

| SAMPLING TIME (min) | I-6 (IOP) | I-8 (TFA-IOP) |
|---|---|---|
| 0 | **** | 0.00 |
| 10 | **** | 863.19 |
| 20 | **** | 603.93 |
| 30 | 556.68 | 573.38 |
| 40 | **** | 510.22 |
| 50 | 507.76 | 469.19 |
| 60 | 462.07 | 414.69 |
| 70 | 462.46 | 373.79 |

TABLE 2-continued

PLASMA:
−IOP CONCENTRATION (uM)

| SAMPLING TIME (min) | I-6 (IOP) | I-8 (TFA-IOP) |
|---|---|---|
| 80 | 403.95 | 403.05 |
| 90 | 372.89 | 359.94 |

****Indicates that no samples were obtained for these time periods.

TABLE 3

BILE:
−IOP CONCENTRATION (uM)

| SAMPLING TIME (min) | I-6 (IOP) | I-8 (TFA-IOP) |
|---|---|---|
| 0 | **** | 635.0 |
| 5 | 1605.8 | 3010.0 |
| 15 | 8659.4 | 5777.6 |
| 25 | 10504.9 | 6436.1 |
| 35 | 9854.3 | 7802.9 |
| 45 | 9667.6 | 7641.1 |
| 55 | 7316.4 | 8461.4 |
| 65 | 7529.1 | 5372.5 |
| 75 | 7758.8 | 5305.7 |
| 85 | 9564.6 | 4663.1 |

****Indicates that no sample was obtained for this time period.

TABLE 4

URINE:
−IOP CONCENTRATION (uM)

| SAMPLING TIME (min) | I-6 (IOP) | I-8 (TFA-IOP) |
|---|---|---|
| 0–20 | 0 | 0 |
| 20–40 | 0 | 0 |
| 40–60 | 0 | *** |
| 60–80 | 0 | *** |
| 80–90 | 0 | *** |

***Indicates that no samples were obtained for these time periods.

TABLE 5

NMR DATA:

| TISSUE | CONTROL VALUE | I-6 (IOP) | I-8 (TFA-IOP) |
|---|---|---|---|
| | T1 VALUES (msec) | | |
| Liver | 214.96 | 228.26 | 243.07 |
| Plasma | 1332.65 | 1406.19 | 1455.34 |
| | T2 VALUES (msec) | | |
| Liver | 38.27 | 28.65 | 28.94 |
| Plasma | 232.18 | 257.87 | 221.56 |

As expected, the values obtained do not significantly differ from control values

TABLE 6

| | TISSUE WEIGHT | % OF B. WT. | uMOLES IN TISS. | uMOLES PER gram | uMOLES PER kg | PERCENTAGE OF DOSE IN TISS. | PERCENTAGE OF DOSE PER gram | PERCENTAGE OF DOSE PER kg b.wt. |
|---|---|---|---|---|---|---|---|---|
| INTRAVENOUS IOP RAT STUDY | | | | | | | | |
| RAT NUMBER: 6 | | | | | | | | |
| DOSE: 104. umoles/kg | | | | | | | | |
| TIME: 90. minutes | | | | | | | | |
| BODY WEIGHT: 406. grams | | | | | | | | |
| LIVER | 11.98 | 2.95 | 6.13 | .51 | 511.90 | 14.52 | 1.21 | 35.77 |
| SPLEEN | .75 | .18 | .19 | .26 | 255.54 | .45 | .61 | 1.12 |
| UPPER GI | 1.79 | .44 | .55 | .31 | 307.91 | 1.31 | .73 | 3.22 |
| LOWER GI | 1.83 | .45 | .25 | .14 | 135.23 | .59 | .32 | 1.44 |
| KIDNEY | 2.76 | .68 | .29 | .11 | 105.40 | .69 | .25 | 1.70 |
| LUNG | 1.57 | .39 | .51 | .32 | 324.91 | 1.21 | .77 | 2.98 |
| HEART | 1.18 | .29 | .31 | .26 | 259.38 | .72 | .61 | 1.79 |
| INTRAVENOUS TFA-IOP RAT STUDY | | | | | | | | |
| RAT NUMBER: 8. | | | | | | | | |
| DOSE: 100. umoles/kg | | | | | | | | |
| TIME: 90. minutes | | | | | | | | |

TABLE 6-continued

| | TISSUE WEIGHT | % OF B. WT. | uMOLES IN TISS. | PER gram | PER kg | PERCENTAGE OF DOSE IN TISS. | PER gram | PER kg b.wt. |
|---|---|---|---|---|---|---|---|---|
| BODY WEIGHT: 435. grams | | | | | | | | |
| LIVER | 13.02 | 2.99 | 2.63 | .20 | 201.73 | 6.04 | .46 | 13.88 |
| SPLEEN | .63 | .14 | .10 | .16 | 164.06 | .24 | .38 | .55 |
| UPPER GI | 1.27 | .29 | .18 | .14 | 140.23 | .41 | .32 | .94 |
| LOWER GI | 1.54 | .35 | .27 | .18 | 178.09 | .63 | .41 | 1.45 |
| KIDNEY | 2.56 | .59 | .15 | .06 | 57.84 | .34 | .13 | .78 |
| LUNG | 1.30 | .30 | .36 | .28 | 277.64 | .83 | .64 | 1.91 |
| HEART | 1.29 | .30 | .31 | .24 | 242.85 | .72 | .56 | 1.66 |

TABLE 7

INTRAVENOUS TFA-IOP RAT STUDY

RAT I.D.: I-8
COMPOUND: TFA-IOP
DOSE: 100. umoles/kg
BODY WEIGHT: 435. grams
UMOLES INJECTED: 43.50 umoles
LIVER WEIGHT: 13.02 grams
EXP. LENGTH: 90 minutes

| SAMPLE PERIOD (min) | BILE FLOW ml/min | ml/min PER kg b.w. | ml/min PER kg l.w. | COMPOUND CONC. (umolar) | EXCRETION umoles/min | umoles/min PER kg b.w. | umoles/min PER kg l.w. | SAMPLE WEIGHT (grams) |
|---|---|---|---|---|---|---|---|---|
| 10-0 | .02093 | .04811 | 1.60753 | 635.0 | .013 | .031 | 1.021 | .20930 |
| 0-10 | .04071 | .09359 | 3.12673 | 3010.0 | .123 | .282 | 9.411 | .40710 |
| 10-20 | .03675 | .08448 | 2.82258 | 5777.6 | .212 | .488 | 16.308 | .36750 |
| 20-30 | .04050 | .09310 | 3.11060 | 6436.1 | .261 | .599 | 20.020 | .40500 |
| 30-40 | .02992 | .06878 | 2.29800 | 7802.9 | .233 | .537 | 17.931 | .29928 |
| 40-50 | .03047 | .07005 | 2.34025 | 7641.1 | .233 | .535 | 17.882 | .30470 |
| 50-60 | .02817 | .06476 | 2.16359 | 8461.4 | .238 | .548 | 18.307 | .28170 |
| 60-70 | .02721 | .06255 | 2.08986 | 5372.5 | .146 | .336 | 11.228 | .27210 |
| 70-80 | .02653 | .06099 | 2.03763 | 5305.7 | .141 | .324 | 10.811 | .26530 |
| 80-90 | .02586 | .05945 | 1.98618 | 4663.1 | .121 | .277 | 9.262 | .25860 |

| SAMPLE PERIOD (min) | UMOLES IN SAMPLE | RUNNING TOTAL | PERCENTAGE OF DOSE IN SAMPLE | RUNNING TOTAL | PER gm. SAMPLE | PER kg. BODY WT. |
|---|---|---|---|---|---|---|
| 10-0 | .13 | .13 | .31 | .31 | 1.46 | .70 |
| 0-10 | 1.23 | 1.36 | 2.82 | 3.12 | 6.92 | 6.48 |
| 10-20 | 2.12 | 3.48 | 4.88 | 8.00 | 13.28 | 11.22 |
| 20-30 | 2.61 | 6.09 | 5.99 | 14.00 | 14.80 | 13.78 |
| 30-40 | 2.33 | 8.42 | 5.37 | 19.36 | 17.94 | 12.34 |
| 40-50 | 2.33 | 10.75 | 5.35 | 24.71 | 17.57 | 12.30 |
| 50-60 | 2.38 | 13.13 | 5.48 | 30.19 | 19.45 | 12.60 |
| 60-70 | 1.46 | 14.60 | 3.36 | 33.56 | 12.35 | 7.73 |
| 70-80 | 1.41 | 16.00 | 3.24 | 36.79 | 12.20 | 7.44 |
| 80-90 | 1.21 | 17.21 | 2.77 | 39.56 | 10.72 | 6.37 |

TABLE 8

INTRAVENOUS IOP RAT STUDY

RAT I.D.: I-6
COMPOUND: IOP
DOSE: 104. umoles/kg
BODY WEIGHT: 406. grams
UMOLES INJECTED: 42.22 umoles
LIVER WEIGHT: 11.98 grams
EXP. LENGTH: 90 minutes

| SAMPLE PERIOD (min) | BILE FLOW ml/min | ml/min PER kg b.w. | ml/min PER kg l.w. | COMPOUND CONC. (umolar) | EXCRETION umoles/min | umoles/min PER kg b.w. | umoles/min PER kg l.w. |
|---|---|---|---|---|---|---|---|
| −10-0 | no sample weight | | | no sample conc. | | | |
| 0-10 | .01375 | .03386 | 1.14750 | 1605.8 | .022 | .054 | 1.843 |
| 10-20 | .00867 | .02136 | .72404 | 8659.4 | .075 | .185 | 6.270 |
| 20-30 | .01077 | .02652 | .89866 | 10504.9 | .113 | .279 | 9.440 |
| 30-40 | .00977 | .02406 | .81528 | 9854.3 | .096 | .237 | 8.034 |
| 40-50 | .01161 | .02861 | .96953 | 9667.6 | .112 | .277 | 9.373 |
| 50-60 | .00904 | .02225 | .75417 | 7316.4 | .066 | .163 | 5.518 |
| 60-70 | .01072 | .02640 | .89457 | 7529.1 | .081 | .199 | 6.735 |
| 70-80 | .01018 | .02506 | .84942 | 7758.8 | .079 | .194 | 6.590 |
| 80-90 | .00977 | .02407 | .81586 | 9564.6 | .093 | .230 | 7.803 |

| SAMPLE PERIOD | SAMPLE WEIGHT | UMOLES IN | RUNNING | PERCENTAGE OF DOSE IN | RUNNING | PER gm. | PER kg. |
|---|---|---|---|---|---|---|---|

TABLE 8-continued
INTRAVENOUS IOP RAT STUDY

RAT I.D.: I-6
COMPOUND: IOP
DOSE: 104. umoles/kg
BODY WEIGHT: 406. grams
UMOLES INJECTED: 42.22 umoles
LIVER WEIGHT: 11.98 grams
EXP. LENGTH: 90 minutes

| (min) | (grams) | SAMPLE | TOTAL | SAMPLE | TOTAL | SAMPLE | BODY WT. |
|---|---|---|---|---|---|---|---|
| −10−0 | | no sample concentration, thus cannot calculate these values | | | | | |
| 0−10 | .13747 | .22 | .22 | .52 | .52 | 3.80 | 1.29 |
| 10−20 | .08674 | .75 | .97 | 1.78 | 2.30 | 20.51 | 4.38 |
| 20−30 | .10766 | 1.13 | 2.10 | 2.68 | 4.98 | 24.88 | 6.60 |
| 30−40 | .09767 | .96 | 3.07 | 2.28 | 7.26 | 23.34 | 5.61 |
| 40−50 | .11615 | 1.12 | 4.19 | 2.66 | 9.92 | 22.98 | 6.55 |
| 50−60 | .09035 | .66 | 4.85 | 1.57 | 11.48 | 17.33 | 3.86 |
| 60−70 | .10717 | .81 | 5.66 | 1.91 | 13.40 | 17.83 | 4.71 |
| 70−80 | .10176 | .79 | 6.45 | 1.87 | 15.27 | 18.38 | 4.61 |
| 80−90 | .09774 | .93 | 7.38 | 2.21 | 17.48 | 22.65 | 5.45 |

What is claimed is:

1. A modified organic contrast analog, comprising alpha-fluoro-N-trifluoroacetyl-iopanoic acid.

* * * * *